United States Patent [19]
King et al.

[11] Patent Number: 5,276,032
[45] Date of Patent: Jan. 4, 1994

[54] VISION AID AND ANESTHETIC COMPOSITION

[76] Inventors: O. Newton King, 2524 Yale Rd.; Henry W. Buck, 306 Homestead Dr., both of, Lawrence, Kans. 66049

[21] Appl. No.: 788,932

[22] Filed: Nov. 7, 1991

Related U.S. Application Data

[63] Continuation of Ser. No. 458,300, Dec. 28, 1989, abandoned.

[51] Int. Cl.$^5$ ............... A61K 31/535; A61K 31/445; A61K 31/24; A61K 47/00
[52] U.S. Cl. ................... 514/239.2; 514/317; 514/535; 514/626; 514/536; 514/781; 514/944; 514/967; 514/969
[58] Field of Search ............... 514/817, 818, 535, 617, 514/619, 626, 317, 239.2

[56] References Cited

U.S. PATENT DOCUMENTS

| | | | |
|---|---|---|---|
| 1,907,392 | 5/1933 | Stover | 514/535 |
| 2,382,546 | 8/1945 | Curtis | 514/535 X |
| 2,803,582 | 8/1957 | Cherney | 514/535 X |
| 3,019,163 | 1/1962 | Harnist et al. | 514/535 X |
| 4,748,022 | 5/1988 | Busciglio | 424/195.1 |

FOREIGN PATENT DOCUMENTS 460629 1/1937 United Kingdom .

*Primary Examiner*—Frederick E. Waddell
*Assistant Examiner*—T. J. Criares

[57] ABSTRACT

A new visualizing and anesthetic composition and the process for the preparation thereof. The composition, generally as a gel, contains an effective amount of a topical anesthetic, an effective amount of a visualizing agent and a pharmaceutically acceptable gelling reservoir as a heat exchanger and/or a light transmitter. The composition is useful for topical application to a region of mammalian skin to supply visualization to a lesion therein and to anesthetize the region for a subsequent destructive therapy.

9 Claims, No Drawings

VISION AID AND ANESTHETIC COMPOSITION

The present application is a continuation of U.S. patent application Ser. No. 07/458,300 filed Dec. 28, 1989, now abandoned.

BACKGROUND OF THE INVENTION

1. Field of the Invention

The present invention relates to a new visualizing and anesthetic composition, and the process for the preparation thereof, which composition possesses useful visualizing and anesthetic activities, and, more particularly, this composition is useful for topical application to a region of mammalian skin to supply visualization to a lesion therein and to anesthetize the region for a subsequent destructive therapy.

History of the Prior Art

Certain viruses and bacteria are known to cause lesions on mammalian skin. Lesions caused by, and associated with, the human papillomavirus (HPV) are commonly known as genital warts, venereal warts or condyloma acuminata. HPV is transmitted sexually. Areas commonly affected include the cervix, vagina and external genitalia of both the female and male. Diseased tissues also develop secondary to the HPV infection. The incidence of HPV infections has increased markedly. Untreated, HPV infection can cause severe complications.

Most of the histopathologic features of HPV-related lesions correspond to the cytopathic effects of HPV on squamous epithelium in different stages of differentiation. Other features include degenerative nuclear alterations (wrinkling, pyknosis, and binucleation) of granular cells and production of excess keratin (hyperkeratosis), particularly in cutaneous warts. These genital warts or lesions are generally treated by destructive therapy, such as cryotherapy or laser vaporization in an office setting.

The prefix "cryo" denotes very low temperature. Extremely low temperature can destroy abnormal tissue. For example, cooling tissue to a temperature of $-80°$ C. will cause the treated tissue to shed off and slough away over time, producing a watery discharge.

In most cases, not only the visible lesions, but also the "invisible" lesions caused by HPV must be treated. The "invisible" lesions normally reside in normal appearing tissue adjacent to the visible lesions. Also, these "invisible" lesions are often flat, not elevated above the surface of the skin. These "invisible" lesions must first be visualized before they can be treated by any destructive therapy.

HPV infection affects the orientation of keratin filaments within the superficial layers of infected squamous epithelium. Application of dilute acetic acid (about 3-5%) to such areas causes the areas to turn white—the so-called acetowhite epithelium. In fact, benign HPV-related infections, the various grades of dysplasia, and carcinomas in situ all manifest acetowhite epithelium, particularly as seen under colposcopic visualization. It has been postulated that acetowhitening of high-grade lesions probably occurs because the osmotic dehydration accentuates the high content of optically dense chromatin in cervical intraepitheline neoplasia. On the other hand, acetowhitening of minor lesions is probably attributable to some transient reaction between acetic acid and abnormal envelope proteins in HPV-infected keratinocytes. Other grades of lesion could reflect a combination of both events. M. Coppleson, "Colposcopic Features of HPV in the Female Genital Tract" in *Obstetrics and Gynecology Clinics of North America*, R. Reid, Ed., Vol. 14/2, June 1987, page 476, R. Reid and P. Scalzi, Am. J. Obstet. Gynecol., Vol. 153, pages 611-618 (1985).

In addition to visualizing the lesion for therapy, some topical or local anesthetics must also be used for the comfort of the patient being treated. The use of these anesthetics is particularly desirable when treating sites which are located on the extremely sensitive external genitalia of either males or females.

Local anesthetic composition is well known in the art. U.S. Pat. No. 2,004,891 to Goldberg teaches anesthetic solution containing procaine acetate and epinephrin. U.S. Pat. No. 3,038,835 to Endres et al. discloses derivatives of 2,6-xylidine as surface anesthetic. Likewise, RESOLVE® is a commercially available product that produces surface anesthesia when applied topically to inflamed or abraded skin or to mucous membrane, such as cold sores. Each gram of RESOLVE® contains 10 mg of dyclonine hydrochloride (4'butoxy-3-piperidinopropiophenone hydrochloride).

Traditionally, the visualizing agent and the local anesthetic agent are applied separately to the regions to be subjected to destructive therapy. Commonly, the regions are "washed" with an aqueous solution of acetic acid to visualize the lesion. Then a topical anesthetic gel/ointment is applied to the same regions to prepare the regions for therapy. Occasionally, a solution of local anesthetic is injected into the regions before the therapy. The separate application of these agents, however, causes undesirable problems and complications. If the aqueous acetic acid is applied first to visualize the lesion and then followed by the application of topical anesthetic agent to induce local anesthesia, the visualizing effect of the acetic acid is hampered by the subsequent application of the anesthetic agent. Consequently, the visualization of lesions previously detected is lost. In fact, even in the absence of any other agent, the visualizing effect of the aqueous acetic acid is short-lived. If more acetic acid is reapplied to the region, the effective concentration of the topical anesthetic is reduced, lessening its anesthetic effect and causing the patient to suffer unnecessary pain.

An alternate way to apply the two agents separately is to first apply the topical anesthetic agent to the suspected region to induce topical anesthesia followed by the application of the aqueous acetic acid to visualize the lesion. However, this is also not an ideal way. Introducing aqueous acetic acid to some topical anesthetic agent usually creates a messy mix on the skin, reducing the effectiveness of the acetic acid and further obscuring the treatment site.

The effect of the traditional way of applying the visualizing agent and the local anesthetic agent separately is loss of visualization of lesions, dilution of the anesthetic effect, and obscuring the surgical field. The net result is less effective treatment of the patient accompanied by suffering greater pain than necessary.

The present invention overcomes the prior art problems as discussed above.

SUMMARY OF THE INVENTION

The present invention relates to a composition for topical application to a region of mammalian skin to supply visualization to a lesion therein and to anesthetize the region for a subsequent destructive therapy.

Broadly, the composition contains: An effective amount of a topical anesthetic to impart local anesthesia around the region; an effective amount of a visualizing agent to visualize and recognize the lesion; and a pharmaceutically acceptable gelling reservoir to give the desired consistency and to provide the necessary heat exchange interface and/or light transmitter.

It is, therefore, an object of the present invention to provide a new water base gel containing an effective amount of topical anesthetic and an effective amount of visualizing agent. When applied to a region of a mammalian skin, the new water base gel supplies visualization to a lesion therein, anesthetizes the region, and provides the necessary medium, namely, a heat transfer interface or a light transmitter for a subsequent cryotherapy or laser ablation, respectively.

It is a further object of the present invention to provide a gel that is a visual aid and is also an anesthetic agent. The gel is characterized in that it is clear and it allows transmissions of light and trans-visualization.

It is another object of the present invention to provide a visual aid and anesthetic gel with a consistency that allows the gel to remain where applied, even on a vertical surface or the underside of a surface.

It is still another object of the present invention to provide a visual aid and anesthetic gel that has a reasonable shelf-life and that can retain its integrity after application on skin surfaces. The gel maintains its therapeutic properties after having been applied on body surfaces for about one hour. It resists drying and also maintains its therapeutic properties necessary for subsequent cryotherapy. Further, the gel retains its therapeutic properties after storage at room temperature for a reasonable period of time.

DESCRIPTION OF PREFERRED EMBODIMENTS

In accordance with this invention there is provided a composition for use in locally visualizing and anesthetizing a region on a mammalian skin having a lesion therein for subsequent destructive therapy. Broadly, the composition contains, an effective amount of a topical anesthetic, an effective amount of visualizing agent, and a heat exchange interface or a light transmitter in the form of a pharmaceutically acceptable gelling reservoir.

Topical anesthetics are compounds which block nerve conduction when applied topically to nerve tissue in appropriate concentrations. They produce reversible loss of sensation by preventing or diminishing the conduction of sensory nerve impulses near the site of their application or action. Their main site of action is the cell membrane. Local anesthetics could also be described as local analgesics as they are most often used to produce loss of pain without loss of nervous control. A preferred local anesthetic should not be irritating to the tissue to which it is applied, nor should it cause any permanent damage to nerve structure. It should have low systemic toxicity because it is eventually absorbed from its site of application. The time required for the onset of anesthesia should be as short as possible. Furthermore, the action must last long enough to allow time for the contemplated surgery or therapy, yet not so long as to entail an extended period of recovery. Local anesthetics, and their acid addition salts, of the ester type suitable for this invention include: Amethocaine (tetracaine, or 2-dimethylaminoethyl 4-butylaminobenzoate); benzocaine (ethyl aminobenzoate, or ethyl 4-aminobenzoate); and cocaine (cocainium chloride). Local anesthetics, and their acid addition salts, of the amide type include: Bupivacaine hydrochloride (($\pm$)-(1-butyl-2-piperidyl)formo-2',6'-xylidide hydrochloride monohydrate); cinchocaine (dibucaine, or 2-butoxy-N (2-diethylaminoethyl)-quinoline-4-carboxamide); etidocaine (($\pm$)-2-(N-ethylpropylamino)butyro-2', 6'-xylidide hydrochloride); lignocaine (lidocaine); mepivacaine (1-methyl-2-piperidyl)formo-2',6'-xylidide hydrochloride); and prilocaine (propylaminopropiono-o-toluidide hydrochloride). Other local anesthetics, and their acid addition salts, include: Butacaine sulphate (3-dibutylaminopropyl 4-aminobenzoate sulphate; butanilicaine phosphate (2-butylamino-6'-chloroaceto-o-toluidide dihydrogen phosphate); butyl aminobenzoate (butyl 4-aminobenzoate); carticaine hydrochloride (methyl 4-methyl-3-(2-propylaminopropionamido)thiophene-2-carboxylate hydrochloride; chloroprocaine hydrochloride (2-diethylaminoethyl 4-amino-2-chlorobenzoate hydrochloride); cyclomethycaine sulphate (3-(2-methylpiperidino)-propyl 4-cyclohexyloxybenzoate hydrogen sulphate); dimethisoquin hydrochloride (2-(3-butyl-1-isoquinolyloxy)-NN-dimethylethyl-amine hydrochloride); diperodon (3-piperidinopropylene bis(phenylcarbamate) monohydrate); dyclonine hydrochloride (4'-butoxy-3-piperidinopropiophenone hydrochloride); ethyl chloride (chloroethane); euprocin hydrochloride ((9R)-10,11-dihydro-6'-(3-methylbutoxy)cinchonan-9-ol dihydrochloride monohydrate); fomocaine (4-[3-(alphaphenoxy-p-tolyl)propyl]morpholine); hexylcaine hydrochloride (2-cyclohexylamino-1-methylethyl benzoate hydrochloride); isobucaine hydrochloride (2-isobutylamino-2-methylpropyl benzoate hydrochloride); ketocaine hydrochloride (2'-(2-di-isopropylaminoethoxy)butyrophenone hydrochloride); leucinocaine mesylate (2-diethylamino-4-methylpentyl 4-aminobenzoate methanesulphonate); meprylcaine hydrochloride (2-methyl-2-propylaminopropyl benzoate hydrochloride); myrtecaine (2-[2-(10-norpin-2-en-2-yl)ethoxy]triethylamine); octacaine hydrochloride (3-diethylaminobutyranilide hydrochloride); oxybuprocaine hydrochloride (2-diethylaminoethyl 4-amino-3-butoxybenzoate hydrochloride); pramoxine hydrochloride (4-[3-(4-butoxyphenoxy)propyl]morpholine hydrochloride); and proxymetacaine hydrochloride (2-diethylaminoethyl 3-amino-4-propoxybenzoate hydrochloride).

The "effective amount" or "pharmacologically effective amount" of a local anesthetic in a unit dose of composition depends upon a number of factors. Included among those factors are the quantity of gelling reservoir used, the amount of visualizing agent present, the quantity of other ingredients when used, and the tolerance for the active ingredient of anesthetic. Effective amount of local anesthetic ranges from about 0.5% to about 30% by weight based on the total weight of the final composition. The section on Local Anaesthetics, Martindale, the Extra Pharmacopoeia, 29th Edition, J. E. F. Reynolds (ed.), Pharmaceutical Press, London, (1989), offers a guide as to suitable ranges of topical anesthetics under each entry. Ranges of representative topical anesthetics are given below:

| Anesthetic | Suitable Range Weight Percent* | Preferred Range Weight Percent* |
|---|---|---|
| lidocaine HCl | 0.5–30 | 2–25 |
| dyclonine HCl | 0.5–3 | 0.5–2 |

| Anesthetic | Suitable Range Weight Percent* | Preferred Range Weight Percent* |
|---|---|---|
| pramoxine HCl | 0.5–3 | 0.5–2 |
| benzocaine | 0.5–25 | 0.5–20 |
| tetracaine HCl | 0.5–3 | 0.5–2 |
| dibucaine HCl | 0.25–3 | 0.25–1 |
| dimethisoquin HCl | 0.2–2 | 0.3–0.5 |
| lidocaine base | 0.5–30 | 2–25 |
| cocaine | 2–20 | 4–10 |

*Weight percent of the total weight of the final composition.

At proper concentrations, the visualizing agents are not excessively irritating to a mammalian skin. They cause color change where the lesions are found so the lesions can be visualized and recognized. Visualizing agents that are useful include acetic acid and hydrochloric acid. The most preferred visualizing agent is acetic acid. Suitable range of glacial acetic acid is from about 0.1% to about 15% by weight based on the total weight of the final composition. The pH of the composition is reduced by the use of the acidic visualizing agent. Suitable and effective range of the pH is from about 2 to 5, and preferably around 3.

Among other functions, the gelling reservoir acts as an interface which is required to provide an efficient means for heat transfer between the cryoprobe and the skin to be treated. The gelling reservoir is a heat exchange interface. The gelling reservoir also acts as a means to allow transmission of light and to aid in providing the final composition with a desired consistency. Generally, this gelling reservoir is in the form of gel, ointment, lotion, paste, jelly, spray, solution, cream, or aerosol. The gelling reservoir is preferably made up of a water-soluble gum or resin, which may have to be dissolved in water if necessary. Water-soluble resins are polymeric materials whose composition enables them either to dissolve or to swell in water. A wide variety of these polymeric compositions are known. They may be classified as nonionic, anionic cationic, or amphoteric, according to their electrolytic behavior in solution, and as natural or synthetic, according to the method by which they are obtained. They alter the properties of aqueous solutions or form films. Functions include dispersion, rheology control, binding, coating, flocculation, emulsification, foam stabilization and protective-colloid action. Representative of these water-soluble gums and resins include: acacia, agar, alginates, alkyl and hydroxyalkylalkylcellulose, bentonite, carbomer, carboxymethylcellulose ("C.M.C."), carboxymethylcellulose sodium ("sodium C.M.C."), carrageenan, powdered cellulose, cholesterol, gelatin, guar gum, gum agar, gum arabic, gum ghatti, gum karaya, gum tragacanth, hydroxyethylcellulose, hydroxypropylcellulose, hydroxypropyl methylcellulose, locust bean gum, methylcellulose, octoxynol 9, oleyl alcohol, pectins, polyacrylamide, poly(acrylic acid) and its homologs, polyethylene glycol, poly(ethylene oxide), polyvinyl alcohol, polyvinylpyrrolidone, propylene glycol monostearate, sodium lauryl sulfate, sorbitan esters, stearyl alcohol, starch and its modifications, tamarind gum, tragacanth, and xanthan gum. Suitable ranges of gelling reservoir vary from about 0.5% to about 10% by weight based on the total weight of the final composition. Ranges of representative gelling reservoir are given below:

| Gelling Reservoir | Suitable Range Weight Percent* | Preferred Range Weight Percent* |
|---|---|---|
| hydroxypropyl methylcellulose | 0.5–10 | 0.5–5 |
| carboxymethylcellulose ("C.M.C.") | 0.5–10 | 0.5–5 |
| sodium C.M.C. | 0.5–10 | 0.5–5 |
| polyvinylpyrrolidone | 0.5–20 | 0.5–30 |

*Weight percent of the total weight of the final composition.

Other agents can be added to the composition to impart additional desirable properties. Thus, for example, a vehicle and/or a humectant may be used. A typical vehicle includes water. It is usually added to make up the weight or volume. A humectant is an agent known to promote the retention of moisture. Glycerin and propylene glycol are suitable humectants. A preferred humectant for this invention is glycerin. Glycerin is relatively inert. It helps to retain the moisture in the final composition of the present invention, particularly when water is used as a carrier or vehicle. Suitable and effective amounts of glycerin range from about 1% to about 20% by weight based on the total weight of the final composition.

The following non-limiting preferred examples illustrate the present invention. The weight percent expressed for each ingredient is the weight percent based on the total weight of the final composition.

EXAMPLE 1

| Ingredient | Weight Percent |
|---|---|
| lidocaine HCl | 20 |
| glacial acetic acid | 5 |
| hydroxypropyl methylcellulose | 1.5 |
| glycerin | 10 |
| water | q.s. to 100* |

*q.s. as much as suffices

The final composition was prepared by first adding glycerin with stirring to water heated to about 75° C. Meanwhile, lidocaine HCl, in powder form, and hydroxypropyl methylcellulose were mixed to obtain a homogenous mixture. The mixture was then added to the stirred heated water solution containing the glycerin. The resultant mixture was cooled to room temperature, about 25° C. Glacial acetic acid was then added to the cooled mixture. The final mixture was cooled to about 5° C. After about overnight to about 24 hours at this temperature, the final mixture turned into a stable gel. The gel could then be stored at room temperature until use.

The finished gel possessed all the desired properties. The finished gel was clear, and allowed transmission of light and trans-visualization. The gel had a consistency that allowed it to remain at a vertical surface when applied to the surface. The viscosity of the finished gel also allowed it to remain, and not flow or drop, when it was applied to an underside of a surface. The finished gel also retained its integrity in that it maintained its characteristics when stored at room temperature for days or when place on body surfaces, resisting drying and maintaining its gel properties necessary for transmitting heat for cryotherapy from the time of application to the time of treatment, usually from about 5 minutes to about 15 minutes.

EXAMPLE 2

Example 1 was repeated replacing the glacial acetic acid with a sufficient amount of 0.1% of hydrochloride acid to reach a similar pH of about 3.

The finished gel had similar characteristics and properties as the one prepared according to the method described for Example 1.

Example 1 was repeated using the ingredients in the following examples. The finished gel had similar characteristics and properties as the one prepared according to the method described for Example 1.

EXAMPLE 3

| Ingredient | Weight Percent |
| --- | --- |
| dyclonine HCl | 1 |
| glacial acetic acid | 5 |
| hydroxypropyl methylcellulose | 1.5 |
| glycerin | 10 |
| water | q.s. to 100* |

*q.s. as much as suffices

EXAMPLE 4

| Ingredient | Weight Percent |
| --- | --- |
| pramoxine HCl | 1 |
| glacial acetic acid | 5 |
| hydroxypropyl methylcellulose | 1.5 |
| glycerin | 10 |
| water | q.s to 100* |

*q.s. as much as suffices

The following examples can be repeated as in Example 1 using the ingredients given below. The finished gel has similar characteristics and properties as the one prepared according to the method described for Example 1.

EXAMPLE 5

| Ingredient | Weight Percent |
| --- | --- |
| tetracaine HCl | 2 |
| glacial acetic acid | 5 |
| hydroxypropyl methylcellulose | 1.5 |
| glycerin | 10 |
| water | q.s. to 100* |

EXAMPLE 6

| Ingredient | Weight Percent |
| --- | --- |
| dibucaine HCl | 1 |
| glacial acetic acid | 5 |
| hydroxypropyl methylcellulose | 1.5 |
| glycerin | 10 |
| water | q.s. to 100* |

EXAMPLE 7

| Ingredient | Weight Percent |
| --- | --- |
| cocaine HCl | 10 |
| glacial acetic acid | 5 |
| hydroxypropyl methylcellulose | 1.5 |
| glycerin | 10 |
| water | q.s. to 100* |

EXAMPLE 8

| Ingredient | Weight Percent |
| --- | --- |
| dyclonine HCl | 1 |
| glacial acetic acid | 5 |
| carboxymethylcellulose | 1.5 |
| glycerin | 10 |
| water | q.s. to 100* |

*q.s. as much as suffices

Ordinarily, only a thin layer of the gel of the present invention is needed to prepare a region on the skin, the treatment site, for cryotherapy. After application of the gel, a physician should wait for about 8-10 minutes before reexamination and undertaking cryotherapy. The continuous effect of the gel of the present invention will enhance the ability to locate lesions. Enough moisture usually remains on skin to provide interface for cryotherapy. If, however, loss of moisture should occur, an additional thin layer of the gel should be applied. Total anesthesia will not occur. Patients will experience a "stinging" sensation which is quite tolerable and of short duration, not more than a few minutes. Treatment sites can then be viewed under magnification (colposcope). After treatment, the gel of the present invention should be allowed to remain to continue topical anesthesia.

Evaluation routines and use of the gel from the present invention in the treatment of external HPV lesions are given below.

EVALUATION AND TREATMENT—FEMALE

To locate the general area of lesions, if any, apply 5% acetic acid to vulva, including vestibule and anus.

Before the evaporation of 5% acetic solution, inspect vulva and anus with magnification (colposcope), possible biopsy (do not mistake papillosis of vestibule for HPV lesions).

If lesions are found, apply a thin layer of the gel of the present invention—use Q—tip® in urethral meatus—to prepare for cryo.

Flood vagina with 5% acetic acid to evaluate cervix and vagina.

Perform colposcopy with ECC and biopsy of suspicious areas; Monsel's solution.

Inspect vagina, possible biopsy (spiking, micropapillations, etc.).

Treat vulva, vestibule, and anus with cryo.

EVALUATION AND TREATMENT—MALE

To locate the general area of lesions, if any, apply 5% acetic acid to penis and scrotum.

Before the evaporation of the 5% acetic acid, inspect penis, including urethral meatus, possible biopsy (do not mistake papillosis of corona for HPV lesions).

Inspect scrotum.

If lesions found, apply a thin layer of the gel of the present invention—use Q—tip® in urethral meatus—to prepare for cryo.

Apply 5% acetic acid to anus to evaluate the general region. Inspect before the evaporation of the 5% acetic acid, possible biopsy.

If lesions found, apply a thin layer of the gel of the present invention to prepare for cryo.

Treat lesions with cryo.

Clinical studies have shown that patients treated with the new composition reported less pain and shorter duration of residual discomfort as compared with those treated with the conventional method of separately applying anesthetic agent and visualizing agent on the skin region having the lesion therein. Thus, it is seen that the gel of the present invention is a great improvement over the prior art discussed in that it is effective and easy to use.

Each and every publication, patent or otherwise, specifically identified in this specification represents a teaching of the understanding of those skilled in the art at the time this invention was made and is herein individually incorporated by reference to the same extent as if it had been physically reproduced in the location and for the purpose as identified by the context in which it is found.

It is thus believed that the operation and construction of the present invention will be apparent from the foregoing description. Although the composition and method shown and described have been characterized as being preferred, it will be obvious that various changes and modifications may be made therein without departing from the spirit and scope of the invention as defined in the following claims.

We claim:

1. A composition for topical application to a region of mammalian skin to supply visualization to a lesion therein and to anesthetize said region for a subsequent destructive therapy, said lesion being characterized as human papillomavirus related, said composition comprising:
   (a) from about 1% to about 20% by weight, based on total weight of said composition, of a topical anesthetic selected from the group consisting of lidocaine HCL, dyclonine HCL, pramoxine HCL, tetracaine HCL, dibucaine HCL, and cocaine HCL to impart local anesthesia around said region;
   (b) from about 0.1% to about 15% by weight, based upon total weight of said composition, of a visualizing agent selected from the group consisting of acetic acid and hydrochloric acid to visualize and recognize said lesion;
   (c) a pharmaceutical gelling reservoir comprising hydroxypropyl methylcellulose, glycerin, and water in an amount of about 0.5% to 10% by weight, based upon the total weight of said composition; and
   (d) said compositions having a pH in the range of about 2 to about 5.

2. The composition of claim 1 wherein said topical anesthetic is 1% by weight dyclonine HCL, said visualizing agent is 5% by weight of glacial acetic acid, said gelling reservoir is 1.5% by weight of hydroxypropyl methycellulose and 10% by weight of glycerin and water.

3. The composition of claim 2 wherein said glacial acetic acid is replaced with a sufficient amount of 0.1% of hydrochloric acid to reach a pH of about 3.

4. The composition of claim 2 wherein said topical anesthetic is about 5% by weight of lidocaine HCL.

5. The composition of claim 2 wherein said topical anesthetic is about 1% by weight of pramoxine HCL.

6. The composition of claim 2 wherein said topical anesthetic is about 2% by weight of tetracaine HCL.

7. The composition of claim 2 wherein said topical anesthetic is about 1% by weight of dibucaine HCL.

8. The composition of claim 2 wherein said topical anesthetic is about 10% by weight of cocaine HCL.

9. The composition of claim 4 wherein said hydroxypropyl methylcellulose is replaced with carboxymethylcellulose.

* * * * *